United States Patent
Chang et al.

(10) Patent No.: US 12,222,253 B2
(45) Date of Patent: Feb. 11, 2025

(54) MEDICAMENT DELIVERY DEVICE DEVELOPMENT EVALUATION SYSTEM

(71) Applicant: SHL MEDICAL AG, Zug (CH)

(72) Inventors: Chun Chang, Stockholm (SE); Chia Cheng Lin, Taoyuan (TW); Sheng-wei Lin, Taoyuan (TW); Hsueh-Yi Chen, New Taipei (TW); Yiju Chen, New Taipei (TW); Wen-Sheng Chien, Taoyuan (TW)

(73) Assignee: SHL MEDICAL AG, Zug (CH)

( * ) Notice: Subject to any disclaimer, the term of this patent is extended or adjusted under 35 U.S.C. 154(b) by 459 days.

(21) Appl. No.: 17/437,786

(22) PCT Filed: Feb. 13, 2020

(86) PCT No.: PCT/EP2020/053681
§ 371 (c)(1),
(2) Date: Sep. 9, 2021

(87) PCT Pub. No.: WO2020/182403
PCT Pub. Date: Sep. 17, 2020

(65) Prior Publication Data
US 2022/0155161 A1    May 19, 2022

(30) Foreign Application Priority Data

Mar. 13, 2019    (EP) .................................... 19162434

(51) Int. Cl.
*G01L 1/22* (2006.01)
*G01L 5/1627* (2020.01)
*G01P 15/00* (2006.01)

(52) U.S. Cl.
CPC .............. *G01L 1/22* (2013.01); *G01L 5/1627* (2020.01); *G01P 15/00* (2013.01)

(58) Field of Classification Search
CPC . G01L 1/22; G01L 5/1627; G01L 1/04; G01P 15/00; A61M 5/3202; A61M 5/162;
(Continued)

(56) References Cited

U.S. PATENT DOCUMENTS

2016/0157816 A1    6/2016 Denny
2017/0332969 A1*   11/2017 Martin .................... A61M 5/20

FOREIGN PATENT DOCUMENTS

EP    2327431 A1 *  6/2011    .......... A61M 5/1452
EP    3366335 A1    8/2018
(Continued)

OTHER PUBLICATIONS

International Search Report and Written Opinion for Int. App. No. PCT/EP2020/053681, mailed Mar. 17, 2020.

*Primary Examiner* — Brandi N Hopkins
(74) *Attorney, Agent, or Firm* — McDonnell Boehnen Hulbert & Berghoff LLP

(57) ABSTRACT

A medicament delivery device development evaluation system is presented having a dummy medicament delivery device comprising at least one force sensor configured to detect an external force applied to the dummy medicament delivery device, processing circuitry configured to receive force measurements from the force sensor, and a storage medium configured to store the force measurements received by the processing circuitry.

19 Claims, 2 Drawing Sheets

(58) Field of Classification Search
CPC ......... A61M 5/172; A61M 5/32; G09B 19/00;
G09G 3/006; G06F 3/011; G06K
19/07773; G16H 20/17; A61B 5/22
See application file for complete search history.

(56) References Cited

FOREIGN PATENT DOCUMENTS

| | | | |
|---|---|---|---|
| EP | 3247427 B1 * | 10/2021 | ........ A61M 5/31535 |
| WO | 2012/155056 A1 | 11/2012 | |
| WO | WO-2016026679 A1 * | 2/2016 | ........ A61M 5/14244 |
| WO | 2016/162298 A1 | 10/2016 | |
| WO | 2017/070391 A2 | 4/2017 | |

\* cited by examiner

MEDICAMENT DELIVERY DEVICE DEVELOPMENT EVALUATION SYSTEM

CROSS REFERENCE TO RELATED APPLICATIONS

The present application is a U.S. National Phase Application pursuant to 35 U.S.C. § 371 of International Application No. PCT/EP2020/053681 filed Feb. 13, 2020, which claims priority to European Patent Application No. 19162434.5 filed Mar. 13, 2019. The entire disclosure contents of these applications are herewith incorporated by reference into the present application.

TECHNICAL FIELD

The present disclosure generally relates to medicament deliver devices.

BACKGROUND

Many medicament delivery devices on the market today are designed with the purpose to allow a user to operate the medicament delivery device. Users of such devices hence administer the medicament themselves.

For users with certain physical conditions such as rheumatism or multiple sclerosis, which impairs the physical ability to interact with objects it is necessary that the medicament delivery device can be operated with ease to enable the user to interact with the medicament delivery device as required. To this end, it is desirable to design medicament delivery devices with such considerations in mind.

SUMMARY

An object of the present disclosure is to provide a medicament delivery device development evaluation system which solves or at least mitigates problems of the prior art.

There is hence provided a medicament delivery device development evaluation system comprising: a dummy medicament delivery device comprising at least one force sensor configured to detect an external force applied to the dummy medicament delivery device, processing circuitry configured to receive force measurements from the force sensor, and a storage medium configured to store the force measurements received by the processing circuitry.

By measuring the external force applied to the dummy medicament delivery device when different beta-test users interact with it, the force(s) required to interact with the device may be determined for example for users with different physical impairments. The conclusions from such measurements may be used to develop a medicament delivery device taking the measurement results into consideration. Medicament delivery devices which can easily be operated by users with specific impaired abilities may thereby be designed.

According to one embodiment the at least one force sensor is a plurality of force sensors.

According to one embodiment the plurality of force sensors includes a rotation force sensor and a linear force sensor.

A rotation force sensor may for example comprise a strain gauge. A linear force sensor may for example comprise a pressure sensor, or an accelerometer.

According to one embodiment, the medicament delivery device development evaluation system includes a plurality of different dummy medicament delivery devices, each including at least one force sensor configured to detect an external force applied to the respective dummy medicament delivery device. The processing circuitry, or a plurality of processing circuitries, may be configured to obtain force measurements from the force sensors of the dummy medicament delivery devices. The storage medium may be configured to store the force measurements received by the one or more processing circuities.

Each dummy medicament delivery device may comprise a main body and a movable member, which is movably connected to the main body. The main body and the movable member of each respective dummy medicament delivery device may form an integral unit. The at least one force sensor of the respective dummy medicament delivery device is configured to measure the force applied to the dummy medicament delivery device when the movable member is moved relative to the main body.

The movable member may for example be rotatable and/or linearly or axially movable relative to main body. The corresponding force sensor may be configured to detect the axial or rotational force applied to the dummy medicament delivery device when the movable member is moved relative to the main body.

According to one embodiment the dummy medicament delivery device is modular and includes a main body module and a plurality of alternative modules of the same module type configured to be detachably assembled with the main body module, wherein the main body module includes the at least one force sensor or each alternative module includes a respective one of the at least one force sensor.

The alternative modules may for example have different dimensions, structures, shapes, and/or be made of different materials. The alternative modules may for example have different surface finish, such as surface roughness and/or surface waviness.

Each alternative module may form a particular component of a medicament delivery device, such as a cap, an activation button or a delivery member shield/cover such as a needle shield/cover.

By allowing a user to interact with the dummy medicament delivery device using different alternative modules of the same module type, an understanding of the best suitable alternative module e.g. with respect to friction between the main body module and the alternative modules may be determined. This conclusion may then be used in the development/design of a medicament delivery device, and in particular of the component corresponding to the alternative module and its mechanical interfacing with the main body module, which typically corresponds to a housing of an actual medicament delivery device.

According to one embodiment the at least one force sensor is configured to detect a force applied to the main body module or to the alternative module by movement of an alternative module, assembled with the main body module, relative to the main body module, and wherein the processing circuitry is configured to receive a force measurement from the at least one force sensor for each alternative module assembled with the main body module, and the storage medium is configured to store the force measurements.

According to one embodiment one module type is a cap, wherein the rotation force sensor is configured to detect a rotational force applied to the main body module or the cap by rotation of the cap relative to the main body module.

According to one embodiment the linear force sensor is configured to detect a linear force applied to the main body module or to the cap when the cap is pulled off the main body module.

According to one embodiment one module type is activation button, wherein the linear force sensor is configured to detect a linear force applied to the activation button.

According to one embodiment the processing circuitry is configured to determine whether the force measurements are within corresponding reference ranges.

According to one embodiment the processing circuitry is arranged within the main body.

According to one embodiment the processing circuitry is arranged in an external computing device.

One embodiment comprises a display device configured to display the force measurements stored in the storage medium.

According to one embodiment the display device is configured to display reference ranges for each of the force measurements stored in the storage medium.

One embodiment comprises a communication device arranged within the main body and configured to transit the force measurements stored in the storage medium to an external device.

According to one embodiment the communication device configured to transit the real time force measurements to an external device.

According to one embodiment the communication device configured to wirelessly or by wire transit the force measurements to an external device.

According to one embodiment the external device comprises a display configured to synchronously display the received real time force measurements.

According to one embodiment each reference range extends between a maximum allowed force value and a minimum allowed force value for the corresponding force measurement.

According to one embodiment each maximum allowed force value and the minimum allowed force value are determined by a standard.

According to one embodiment the dummy medicament delivery device is a dummy injector, a dummy inhaler or a dummy eye-dispenser.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
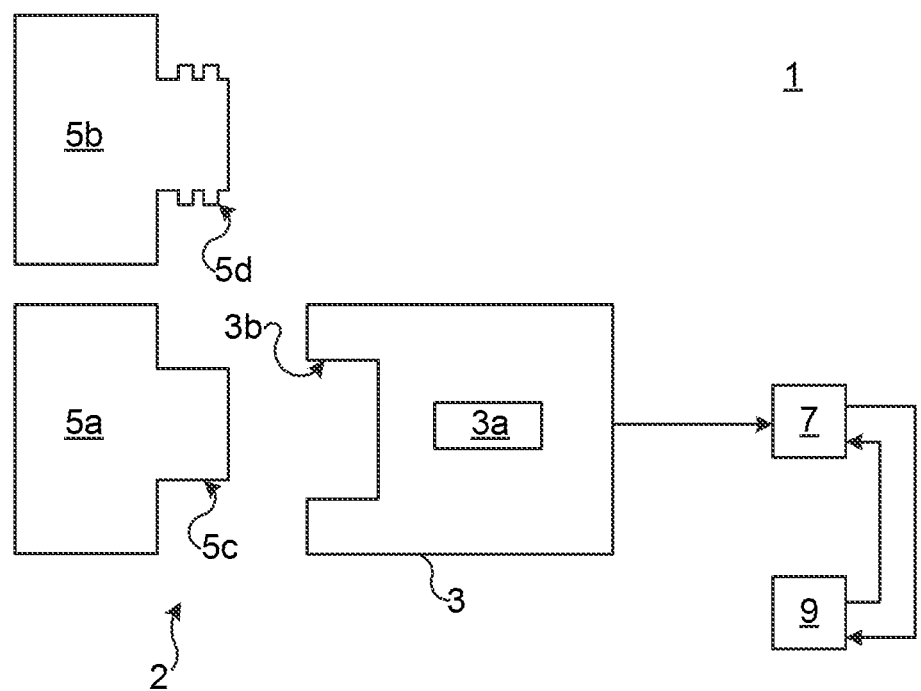
FIG. 1 schematically shows an example of a medicament delivery device development evaluation system.

FIG. 1 depicts an example of a medicament delivery device development evaluation system 1. The exemplified medicament delivery device development evaluation system comprises a dummy medicament delivery device 2. The dummy medicament delivery device 2 may for example be a dummy injector, a dummy inhaler or a dummy eye-dispenser.

The dummy medicament delivery device 2 depicted in FIG. 1 is modular.

The dummy medicament delivery device 1 comprises a main body module 3, and a plurality of alternative modules 5a, 5b of the same module type.

The alternative modules 5a, 5b are configured to be assembled with or attached to the main body module 3. The alternative modules 5a, 5b are configured to be detachable attached to the main body module 3. The main body module 3 may for example correspond to the part of an actual medicament delivery device which contains a medicament container. This part is typically the housing.

The dummy medicament delivery device 1 may according to one variation comprise a plurality of sets of alternative modules. The members of the same set of alternative modules may in this case be of the same module type. The members of different sets of alternative modules may in this case be different. Each set may hence comprise alternative modules of a certain module type. For example, some alternative modules 5a-5b may be different realisations of a cap, some alternative modules may be realisations of different activation buttons, and/or some alternative modules may be realisations of different delivery member covers such as needle shields/covers.

The main body module 3 has a mechanical main body module interface 3b configured to interact with the alternative modules 5a, 5b of a certain module type. Each alternative module 5a, 5b has a mechanical alternative module interface 5c, 5d configured to interact with the main body module interface 3b. Each alternative module interface 5c, 5d may differ from the other alternative module interfaces 5c, 5d. For example the alternative module interface 5c of the alternative module 5a differs from the alternative module interface 5d of the alternative module 5b. This difference may for example be due to the alternative module interfaces 5c, 5b having different dimensions, different structure and/or due to being made of different materials.

The main body module 3 may according to some examples be provided with a plurality of different mechanical main body module interfaces. Each main body module interface may be configured to interact with a respective module type of alternative module and its corresponding alternative module interface. For example, a first main body module interface may be configured for a module type that is a cap, a second main body module interface may be configured for a module type that is an activation button, and a third main body module interface may be configured for a module that that is a delivery member cover e.g. a needle shield/cover.

According to the example shown in FIG. 1, the main body module 3 comprises one or more force sensors 3a. The one or more force sensors 3a is/are configured to detect an external force applied to the dummy medicament delivery device 2. Especially, the one or more force sensors 3a is/are configured to detect a force applied to the dummy medicament delivery device 1 when a user removes or attaches an alternative module 5a, 5b from/to the main body module 3 or when a user actuates an alternative module 5a, 5b fitted to the main body module 3.

The one or more force sensors 3a may for example be a rotation force sensor and/or a linear force sensor.

An alternative module 5a, 5b may according to one example be configured to be attached and detached/removed from the main body module 3 by means of rotating motion. A rotation force sensor may be configured to detect rotational force applied to the dummy medicament delivery device 1 caused by removing an alternative module 5a, 5b by means of rotation relative to the main body module 3. Such an alternative module may for example be a cap or cap module.

An alternative module 5a, 5b may according to one example be configured to be attached and detached/removed from the main body module 3 by means of linear motion or configured to be moved linearly relative to the main body module 3. A linear force sensor may be configured to detect linear force applied to the dummy medicament delivery device 1 caused by removing or moving an alternative module 5a, 5b by means of linear motion relative to the main body module 3. Such an alternative module may for example be an activation button or activation button module, or a delivery member cover or delivery member cover module.

The exemplified medicament delivery device development evaluation system 1 furthermore comprises processing circuitry 7 configured to obtain force measurements from the one or more force sensors 3a. The processing circuitry 7 may be configured to obtain the force measurements from the one or more force sensors 3a by wired connection or wirelessly. The medicament delivery device development evaluation system 1 also comprises a storage medium 9. The storage medium 9 is configured to store the force measurements received by the processing circuitry 7.

The processing circuitry 7 may for example use any combination of one or more of a suitable central processing unit (CPU), multiprocessor, microcontroller, digital signal processor (DSP), application specific integrated circuit (ASIC), field programmable gate arrays (FPGA) etc., capable of executing any herein disclosed operations concerning the handing of force measurements from the one or more force sensors.

The storage medium 9 may for example be embodied as a memory, such as a random access memory (RAM), a read-only memory (ROM), an erasable programmable read-only memory (EPROM), or an electrically erasable programmable read-only memory (EEPROM) and more particularly as a non-volatile storage medium of a device in an external memory such as a USB (Universal Serial Bus) memory or a Flash memory, such as a compact Flash memory.

The storage medium 9 may for example be provided in a device comprising a force measurement application or program. Such a device may for example be a personal computer, a smart phone or a tablet computer. The processing circuitry 7 may according to one variation be provided in the same device as the storage medium 9 or the storage medium 9 may be integral with the processing circuitry 7. Alternatively, the processing circuitry 7 and the storage medium 9 may be provided in different devices/locations e.g. in a cloud or a remote computing device. The processing circuity 7 and the storage medium 9 may be configured to communicate by wired connection or wirelessly with each other. According to other variations, the processing circuitry 7 may be provided in the main body module 3 or alternatively, the processing circuitry 7 and the storage medium 9 may be provided in the main body module 3.

In use of the medicament delivery device development evaluation system 1, one or more test users may be asked to interact with the dummy medicament delivery device 2. The test users may be asked to remove an alternative module 5a, 5b from the main body module 3, e.g. if the alternative module 5a, 5b is a cap. This procedure may be repeated for a plurality of different alternative modules 5a, 5b fitted one after the other to the main body module 3. The one or more force sensors 3a measures the forces applied to the dummy medicament delivery device 2 during user interaction, and sends the force measurements to the processing circuitry 7. The force measurements are stored in the storage medium 9. An optimal amount of friction between the main body module interface 3b and the alternative module interface 5c, 5d may thereby be determined and used for designing medicament delivery devices.

The alternative modules 5a, 5b may in one example include different activation buttons. In this case, the test users may push or slide the activation buttons to simulate activation triggering of a medicament delivery device and hence initiation of medicament administration. The test users may be asked to interact with several alternative modules 5a, 5b in the form of activation buttons that may be assembled with the main body module 3 sequentially. The one or more force sensors 3a measures the applied forces and sends the force measurements to the processing circuitry 7. The force measurements are stored in the storage medium 9. The force measurements may be used by the developers to design an activation button mechanism which can be used with ease by individuals with impaired physical abilities.

The alternative modules 5a, 5b may in one example include different delivery member covers or needle shields/covers which are movably assembled with the main body module 3. In this case, the test users may be asked to press the dummy medicament delivery device 2 towards an imagined injection site with various needle shield/covers assembled with the main body module 3, whereby the alternative module in the form of the delivery member cover/needle shield is moved axially relative to the main body module 3. The force measurement may in this case concern the force with which the dummy medicament delivery device 1 has to be pressed towards the injection site to move the alternative module, i.e. the needle shield. The one or more force sensors 3a measures the applied forces and sends the force measurements to the processing circuitry 7. The force measurements are stored in the storage medium 9.

The medicament delivery device development evaluation system 1 may according to one example comprise a display device configured to display the force measurements stored in the storage medium 9.

According to one example the processing circuitry 7 is configured to determine whether the force measurements obtained from the one or more force sensors 3a are within corresponding reference ranges. For example, the processing circuitry 7 may be configured to compare a force measurement made by a rotation force sensor with a reference range of rotational force values.

Each reference range may have end points corresponding to the maximum allowed force value and minimum allowed force value for a particular force measurement, e.g. for a rotational force measurement and a linear force measurement. The maximum allowed force value and the minimum allowed force value may for example be determined by a standard, such as an ISO standard related to medicament delivery devices. In this manner, it can be determined whether a particular solution of a cap or a button, i.e. an alternative module of a certain type can be used in a medicament delivery device or whether modification of the design is necessary.

The display device may be configured to display the reference ranges for each type of force measurement. The display device may furthermore be configured to display the force measurements simultaneously with the reference ranges.

Figure 2:
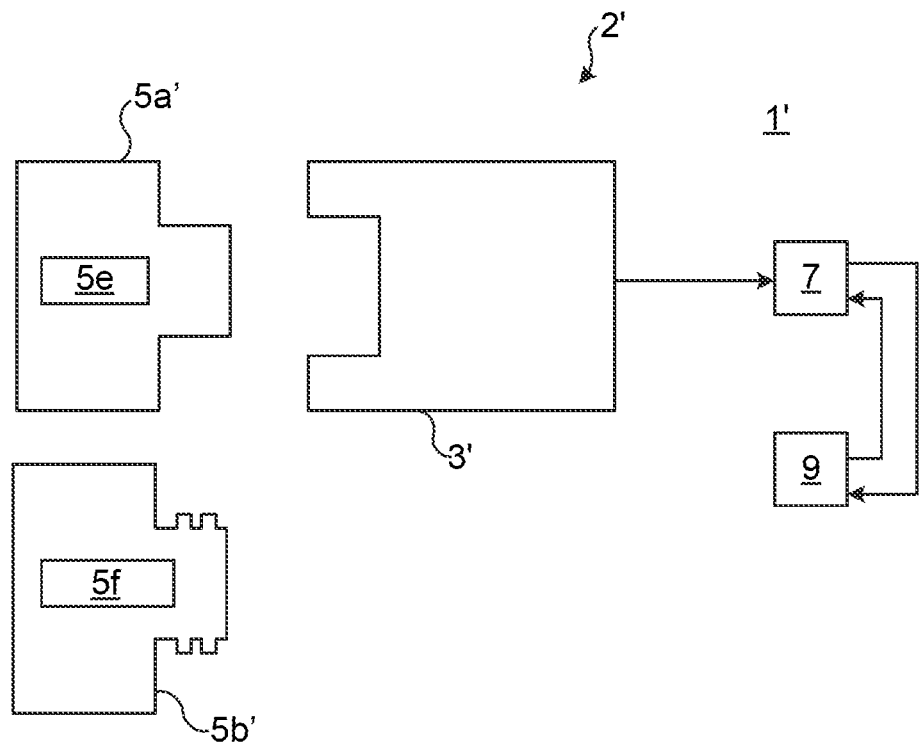
FIG. 2 schematically shows another example of a medicament delivery device development evaluation system.

FIG. 2 shows another example of a medicament delivery device development evaluation system 1'. The medicament delivery device development evaluation system 1' is similar to the medicament delivery device development evaluation system 1 depicted in FIG. 1. A difference compared to the dummy medicament delivery device 2 is that for the dummy medicament delivery device 2' each alternative module 5a', 5b' comprises a respective force sensor 5e, 5f. The main body module 3' of the depicted example does not comprise any force sensor according to this example. According to a variation of the example shown in FIG. 2, the main body module 3' may however also comprise a force sensor (not shown). The force sensors 5e, 5f of the alternative modules 5a', 5b' are configured to communicate with the processing circuitry 7. This communication may for example be wireless, or it may be provided by means of a wired connection with each alternative module 5a', 5b', or the force sensors 5e, 5f may be set in electrical connection with the processing circuitry 7 via the main body module 3' when the corresponding alternative module 5a', 5b' is assembled with the main body module 3'.

Figure 3:
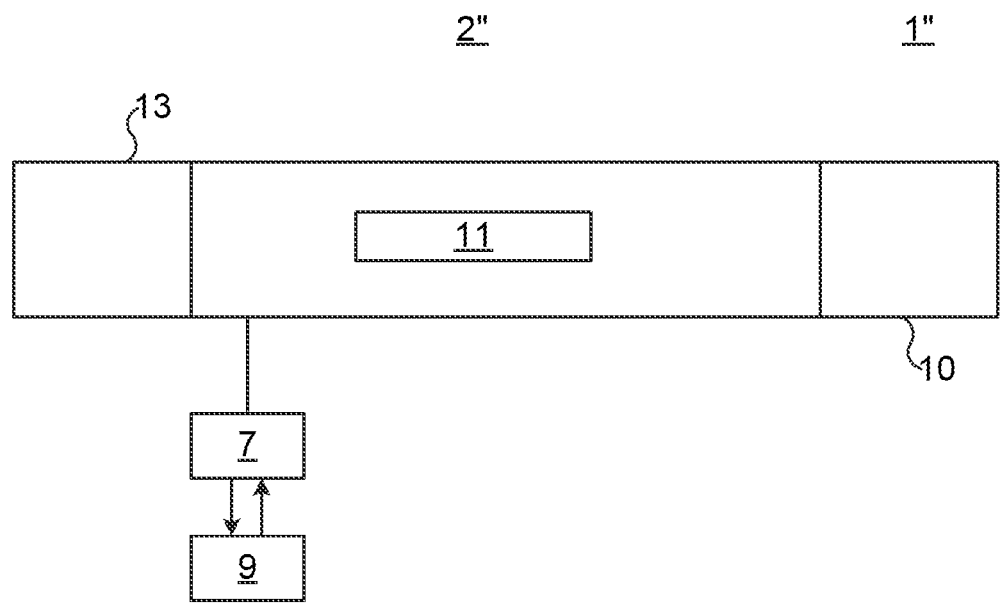
FIG. 3 schematically shows another example of a medicament delivery device development evaluation system.

FIG. 3 shows another example of a medicament delivery device development evaluation system 1". In this example, the dummy medicament delivery device 2" is non-modular. The medicament delivery device development evaluation system 1" may comprise a plurality of different dummy medicament delivery devices 2" of the type explained in the following. The dummy medicament delivery device 2" is designed with non-detachable components, except for the cap in examples in which the dummy medicament delivery device 2" has a cap 10. Hence, according to this example, which has an activation button 13 may must not necessarily have an activation button, the activation button 13 is fixedly mounted to the dummy medicament delivery device 2". The dummy medicament delivery device 2" may comprise one or more force sensors 11, such as rotation force sensors and/or linear force sensors, configured to detect an external force applied to the dummy medicament delivery device 2". The one of more force sensors 11 may be contained in a main body of the dummy medicament delivery device 2". Alternatively, or additionally, one or more force sensor may be contained in e.g. the cap 10 and/or the activation button 13 and/or a delivery member cover. The one or more force sensors 11 are configured to send the force measurements to the processing circuitry 7. The force measurements are stored in the storage medium 9.

Figure 4:
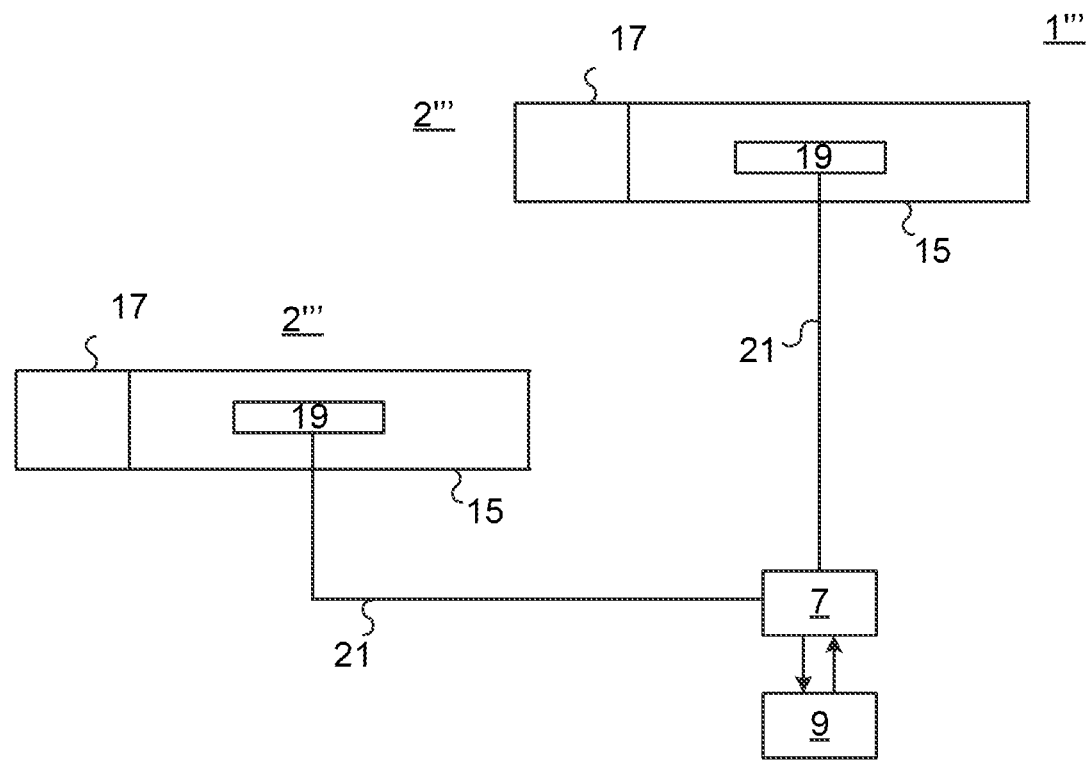
FIG. 4 schematically shows yet another example of a medicament delivery device development evaluation system.

FIG. 4 shows yet another example of a medicament delivery device development evaluation system 1'''. The exemplified medicament delivery device development evaluation system 1''' comprises a plurality of different dummy medicament delivery devices 2'''. Each dummy medicament delivery device 2' comprises a main body 15 and at least one movable member 17 which is movable connected to the main body 15. The main body 15 and the movable member 17 may form an integral unit. The main body 15 and the movable member 17 may hence not be detachable from each other. The movable member 17 may for example be rotatable relative to the main body 15 and/or be linearly movable relative to the main body 15. The movable member 15 may hence be movable along the axial direction of the corresponding dummy medicament delivery device 2'''. The movable member 17 may for example be a cap or an activation button.

The movable member 17 and/or the main body 15 of the various dummy medicament delivery devices 2''' may for example have different dimensions, structures, shapes, and/or be made of different materials. The friction between the main body 15 and the movable member 17 will therefore be different for each dummy medicament delivery device 2'''.

Each dummy medicament delivery device 2''' is provided with at least one force sensor 19. The force sensor may for example be a rotation force sensor or a linear force sensor. According to one example, each dummy medicament delivery device 2''' comprises at least two forces sensors, such as a rotation force sensor and a linear force sensor. The forces sensor(s) of a dummy medicament delivery device 2''' is configured to detect an external force applied to the dummy medicament delivery device 2''' when the movable member 17 is moved relative to the main body 15. The force measurements obtained by the force sensor(s) may be sent to processing circuitry 7, and further to a storage medium 9 of the medicament delivery device development evaluation system 1'''. The processing circuitry 7 and the storage medium 9 may for example be central to all of the dummy medicament delivery devices 2''', i.e. all of the forces sensors 19 of the dummy medicament delivery devices may send the forces measurements to a single processing circuitry 7 by a wired or wireless connection 21. Alternatively, each dummy medicament delivery device 2''' may have its own processing circuitry and/or storage medium.

In use, a beta-test user may be asked to interact with a plurality of the different dummy medicament delivery devices 2'''. This interaction, in particular, the forces measurements detected by the force sensor(s), applied to the dummy medicament delivery devices 2''' by the user, may be stored in the storage medium 9 for analysis.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery device development evaluation system comprising:
   a dummy medicament delivery device comprising a plurality of modular units including a main body module and alternative modules, each configured to be detachable to the main body module, wherein each alternative module of the alternative modules differs from a remainder of the alternative modules, and wherein the main body module comprises one or more force sensors configured to detect an external force applied to the dummy medicament delivery device;
   processing circuitry configured to receive force measurements from the one or more force sensors, wherein the processing circuitry is configured to compare the force measurements to corresponding reference ranges in order to determine whether the force measurements are within the corresponding reference ranges; and a storage medium configured to store the force measurements received by the processing circuitry.

2. The medicament delivery device development evaluation system as claimed in claim 1, wherein the one or more force sensors include a rotation force sensor and a linear force sensor.

3. The medicament delivery device development evaluation system as claimed in claim 1, comprising a plurality of different dummy medicament delivery devices, each dummy medicament delivery device including one or more force sensors configured to detect an external force applied to the respective dummy medicament delivery device.

4. The medicament delivery device development evaluation system as claimed in claim 1, wherein the alternative modules are of the same module type configured to be detachably assembled with the main body module.

5. The medicament delivery device development evaluation system as claimed in claim 4, wherein the one or more force sensors are configured to detect a force applied to the main body module or to the alternative module by movement of an alternative module, assembled with the main body module, relative to the main body module, and wherein the processing circuitry is configured to receive a force measurement from the one or more force sensors, and the storage medium is configured to store the force measurements.

6. The medicament delivery device development evaluation system as claimed in claim 5, wherein one module type is a cap, wherein the one or more force sensors includes a rotation force sensor configured to detect a rotational force applied to the main body module or the cap by rotation of the cap relative to the main body module.

7. The medicament delivery device development evaluation system as claimed in claim 6, wherein the one or more force sensors includes a linear force sensor configured to detect a linear force applied to the main body module or to the cap when the cap is pulled off the main body module.

8. The medicament delivery device development evaluation system as claimed in claim 5, wherein one module type is an activation button, wherein the one or more force sensors includes a linear force sensor is configured to detect a linear force applied to the activation button.

9. The medicament delivery device development evaluation system as claimed in claim 4, wherein each alternative module includes one or more additional force sensors.

10. The medicament delivery device development evaluation system as claimed in claim 1, comprising a display device configured to display the force measurements stored in the storage medium.

11. The medicament delivery device development evaluation system as claimed in claim 10, wherein the display device is configured to display reference ranges for each of the force measurements stored in the storage medium.

12. The medicament delivery device development evaluation system as claimed in claim 11, wherein each reference range extends between a maximum allowed force value and a minimum allowed force value for the corresponding force measurement.

13. The medicament delivery device development evaluation system as claimed in claim 12, wherein each maximum allowed force value and the minimum allowed force value are determined by a standard.

14. The medicament delivery device development evaluation system as claimed in claim 1, wherein the dummy medicament delivery device is a dummy injector, a dummy inhaler or a dummy eye-dispenser.

15. A medicament delivery device development evaluation system comprising:
   a dummy medicament delivery device comprising a plurality of modular units including a main body module and alternative modules, each configured to be detachable to the main body module, wherein each alternative module of the alternative modules differs from a remainder of the alternative modules;
   a rotational force sensor and a linear force sensor both of which is configured to detect an external force applied to the dummy medicament delivery device;
   processing circuitry configured to receive rotational force measurements from the rotational force sensor and receive linear force measurements from the linear force sensor, wherein the processing circuitry is configured to compare the rotational force measurements and the linear force measurements to corresponding reference ranges in order to determine whether the rotational force measurements and linear force measurements are within the corresponding reference ranges; and
   a storage medium configured to store the force measurements received by the processing circuitry.

16. The medicament delivery device development evaluation system as claimed in claim 15, wherein one of the modular units is configured as a cap such that the rotation force sensor detects a rotational force applied to the main body module or to the cap by rotation of the cap relative to the main body module.

17. The medicament delivery device development evaluation system as claimed in claim 15, wherein one of the modular units is configured as an activation button such that the linear force sensor detects a linear force applied to the main body module or to the cap when the cap is pulled off the main body module.

18. The medicament delivery device development evaluation system as claimed in claim 15 further comprises a display device that displays the force measurements stored in the storage medium.

19. The medicament delivery device development evaluation system as claimed in claim 18, wherein the display shows reference ranges for each of the force measurements stored in the storage medium, a maximum allowed force value, and a minimum allowed force value.

* * * * *